United States Patent [19]

Shug et al.

[11] Patent Number: 5,030,458

[45] Date of Patent: * Jul. 9, 1991

[54] METHOD FOR PREVENTING DIET-INDUCED CARNITINE DEFICIENCY IN DOMESTICATED DOGS AND CATS

[76] Inventors: Austin L. Shug, 1201 Shorewood Blvd., Madison, Wis. 53705; Bruce W. Keene, North NC State University College of Veterinary Medicine, 4700 Hillsbourough St., Raleigh, N.C. 27606

[*] Notice: The portion of the term of this patent subsequent to Nov. 28, 2006 has been disclaimed.

[21] Appl. No.: 441,110

[22] Filed: Nov. 27, 1989

[51] Int. Cl.5 .............................................. A23K 1/00
[52] U.S. Cl. ........................................ 426/2; 426/623; 426/630; 426/805; 514/556
[58] Field of Search ................... 426/2, 623, 630, 805; 514/556

[56] References Cited

U.S. PATENT DOCUMENTS 4,382,092  5/1983  Cavazza ............................... 514/556
4,883,672  11/1989  Shug et al. ........................... 426/635

Primary Examiner—R. B. Penland
Attorney, Agent, or Firm—Carl E. Gulbrandsen

[57] ABSTRACT

A method is described for preventing diet-induced Carnitine deficiency in domesticated dogs and cats. A daily prophylactic amount of gamma-butyrobetaine is administered to the pet either as a dietary supplement in an amount of 1.0 to 5.0 grams of gamma-butyrobetaine per day, or gamma-butyrobetaine is provided as an additional ingredient to a commercial pet food in an amount of 1.0 to 5.0 grams of gamma-butyrobetaine per kilogram pet food.

7 Claims, No Drawings

METHOD FOR PREVENTING DIET-INDUCED CARNITINE DEFICIENCY IN DOMESTICATED DOGS AND CATS

GENERAL FIELD OF THE INVENTION

The invention relates to the field of pet food compositions and more specifically to pet food enriched with L-Carnitine.

BACKGROUND OF THE INVENTION

L-Carnitine is a quaternary amine that promotes beta-oxidation of long-chain fatty acids by facilitating their transfer across the mitochondrial membrane. L-Carnitine has also been shown to promote oxidation of branched-chain amino acids and the utilization of acetyl-coenzyme A.

In mammalian species, L-Carnitine concentration in cardiac and skeletal muscle is much higher than in serum. In these tissues fatty acids are utilized as a major source of energy. Because of L-Carnitine's central role in transporting fatty acids to the site of oxidation, adequate levels of L-Carnitine are required for normal fatty acid and energy metabolism in mammalian hearts. This is evidenced by the restoration to normal of fatty acid oxidation in muscle homogenates of certain L-Carnitine deficient patients. A relationship between deficient levels of myocardial L-Carnitine and cardiomyopathy has been observed in both hamsters and dogs. Restoration toward normal of such deficient L-Carnitine levels has been shown to result in improved myocardial function in both species.

In mammals, L-Carnitine is derived from the diet and from biosynthesis in the liver, and in some species, kidney and other tissues. Neither cardiac nor skeletal muscle is capable of synthesizing L-Carnitine, however. Thus, the L-Carnitine found in these tissues was either absorbed from the diet or biosynthesized endogenously by other tissues.

The present invention is for a method of preventing diet-induced carnitine deficiency in domesticated dogs and cats using a dietary supplement containing a prophylactic amount of L-Carnitine. The invention is useful in preventing L-Carnitine deficiencies which can lead to a multitude of conditions, including myopathic heart disease, ischemic heart disease, hyperlipidemia, ketosis, muscle weakness and premature aging.

Pets, particularly the carnivores, are at great risk for developing L-Carnitine deficiencies. As Table 1 indicates, dog and cat foods are extremely low in free L-Carnitine levels as compared with that found in raw ground beef. Most pets are maintained strictly on commercial pet food diets and are thus kept chronically deficient in L-Carnitine. Additionally, applicants' own investigations have found that renal reabsorption of L-Carnitine in dogs ranges from 40% to 95% with the average approximately 75% depending to some extent on diet. This is in marked contrast to the human which has a renal reabsorption approaching 100%. The less efficient renal reabsorption in dogs means that L-Carnitine is lost in the urine. This combined with a diet deficient in L-Carnitine results in a diet-induced carnitine deficiency.

TABLE 1

| LEVEL OF FREE L-CARNITINE IN PET FOODS | |
|---|---|
| SAMPLE IDENTIFICATION | FREE L-CARNITINE "WATER SOLUBLE FRACTION" nanomoles/gram of product |
| GROUND BEEF | 3000.0 |
| ** SAMPLE TYPE: DRY DOG FOOD | |
| ALPO BEEF FLAVORED DINNER 5 LBS | 214.2 |
| CARNATION COME N GET IT 4 LBS | 53.6 |
| GAINES GRAVY TRAIN BEEF FLAVOR 5 LBS | 89.4 |
| KALKAN MEALTIME SMALL CRUNCHY BITS 5 LBS | 105.9 |
| KEN-L-RATION LOVE ME TENDER CHUNKS-BEEF | 27.3 |
| KEN-L-RATION KIBBLES 'N BITS 4 LBS | 78.6 |
| PETTS BRAND ALL NATURAL (HUBBARD) 4 LBS | 167.7 |
| PURINA DOG CHOW 5 LBS | 161.0 |
| PURINA CHUCKWAGON DOG CHOW | 72.7 |
| PURINA HI-PRO 5 LBS | 93.2 |
| PURINA BUTCHER'S BLEND BEEF, BACON, LIVER | 106.3 |
| PURINA FIT AND TRIM 4.5 LBS | 103.9 |
| PURINA PUPPY CHOW 5 LBS | 136.0 |
| NUTRO MAX PUPPY KIBBLE PUPPY FOOD | 143.5 |
| NUTRO MAX KIBBLE DOG FOOD | 192.7 |
| IAMS MINI CHUNKS | 182.9 |
| EUKANUBA (BY IAMS) | 216.3 |
| ** SAMPLE TYPE: SEMI-MOIST DOG FOOD | |
| GAINES BURGERS - BEEF 36 OZ | 55.5 |
| KEN-L-RATION SPECIAL CUTS 24 OZ | 59.2 |
| ** SAMPLE TYPE: CANNED DOG FOOD | |
| ALPO BEEF & LIVER DINNER 14 OZ | 222.8 |
| ALPO LAMB CHUNKS | 89.2 |
| CARNATION MIGHTY DOG BEEF 6.5 OZ | 1799.1 |
| CARNATION MIGHTY DOG TURKEY & GIBLETS | 172.3 |
| GAINES CYCLE 2 (ADULT) BEEF 14 OZ | 28.6 |
| GAINES CYCLE 1 (PUPPY) 14 OZ | 208.9 |
| KALKAN CHOPPED MEATY COMBO 14 OZ | 129.7 |
| KEN-L-RATION CHICKEN, BEEF, LIVER DINNER | 33.9 |
| KEN-L-RATION CHICKEN DINNER | 30.2 |
| RECIPE HEARTY MEAT DINNER 14 OZ | 95.5 |
| VETS-BEEF FLAVORED 15 OZ | 62.5 |
| ** SAMPLE TYPE: DRY CAT FOOD | |

TABLE 1-continued
LEVEL OF FREE L-CARNITINE IN PET FOODS

| SAMPLE IDENTIFICATION | FREE L-CARNITINE "WATER SOLUBLE FRACTION" nanomoles/gram of product |
|---|---|
| KALKAN CRAVE 18 OZ | 135.7 |
| CARNATION FRISKIES OCEAN FISH FLAVOR | 168.6 |
| STARKIST 9 LIVES CRUNCHY MEALS REAL TUNA & EGG | 114.0 |
| IAMS CAT FOOD 26 OZ | 196.9 |
| PURINA CAT CHOW 22 OZ | 109.1 |
| PURINA KITTEN CHOW 18 OZ | 121.4 |
| PURINA MEOW MIX 18 OZ | 61.2 |
| PURINA TENDER VITTLES MOIST CHICKEN DINNER | 127.8 |
| PURINA THRIVE 18 OZ | 95.2 |
| PURINA SPECIAL DINNERS SEA NIP DINNER 18 OZ | 188.2 |
| ** SAMPLE TYPE: CANNED CAT FOOD | |
| STARKIST AMORE TURKEY & GIBLET DINNER 3 OZ | 94.0 |
| STARKIST AMORE POACHED SALMON DINNER 3 OZ | 101.2 |
| CARNATION FRISKIES BUFFET TURKEY & GIBLET 6 OZ | 80.0 |
| CARNATION FRISKIES BUFFET SEAFOOD SUPPER 6 OZ | 180.5 |
| CARNATION FANCY FEAST BEEF & LIVER GOURMET 3 OZ | 364.6 |
| CARNATION FANCY FEAST FANCY SEAFOOD FEAST 3 OZ | 115.4 |
| KALKAN TENDER TURKEY DINNER 6 OZ | 142.0 |
| STARKIST 9 LIVES LIVER & CHICKEN DINNER 6 OZ | 64.5 |
| STARKIST 9 LIVES OCEAN WHITEFISH DINNER 6 OZ | 134.3 |
| PURINA 100 TUNA 6 OZ | 294.3 |
| PURINA BEEF & LIVER DINNER 6 OZ | 595.6 |

EXAMPLE 1

Six apparently healthy Greyhound dogs were determined to be normal by physical examination, fecal flotation, complete blood count, serum biochemical profile, ECG, and echocardiography. They were fed a standard commercial dog food diet free choice for a one-month control period. Control plasma samples (as well as subsequent test samples) were obtained following an eight-hour fast on two consecutive days for analysis of total, free, and esterified L-Carnitine concentration. The average of the plasma L-Carnitine concentration on two consecutive days was taken for each dog and each measuring period.

Following the control period, all of the dogs were continued for two weeks on the standard commercial dog food diet supplemented with L-Carnitine. The L-Carnitine supplement was in the form of 0.5 kg per dog per day of raw frozen lean ground beef. This was equivalent to a daily supplement of 350 mg. of L-Carnitine per dog. Plasma samples were drawn on days 7 and 8 (averaged for the one-week measurement) and days 13 and 14 (averaged for the two-week measurement) for L-Carnitine analysis. Differences between the means of each test period and control were determined by the Student's t test.

RESULTS

The results of the study are shown in Table 2.

TABLE 2

| Dog # | PLASMA CARNITINE CONCENTRATIONS. U MOLES/LITER. | | | | | | | | |
|---|---|---|---|---|---|---|---|---|---|
|   | Control | | | Week 1 | | | Week 2 | | |
|   | Total | Free | Ester | Total | Free | Ester | Total | Free | Ester |
| 1 | 29.6 | 25.0 | 4.5 | 70.1 | 58.9 | 11.2 | 52.4 | 44.9 | 8.0 |
| 2 | 38.7 | 32.2 | 6.5 | 70.7 | 60.5 | 10.2 | 65.7 | 62.2 | 3.5 |
| 3 | 27.2 | 26.1 | 1.2 | 57.2 | 52.5 | 4.7 | 58.1 | 52.7 | 2.2 |
| 4 | 31.9 | 30.5 | 1.4 | 63.1 | 55.6 | 3.4 | 56.3 | 52.0 | 4.3 |
| 5 | 23.1 | 20.0 | 3.1 | 58.1 | 56.0 | 2.1 | 66.3 | 58.5 | 8.7 |
| 6 | 27.6 | 23.4 | 4.2 | 56.3 | 51.7 | 4.8 | 43.2 | 41.0 | 2.2 |
| AVG | 31.8 | 26.2 | 3.4 | 62.5* | 55.9** | 6.0 | 57.0 | 51.9* | 4.8 |
| S.D. | ±5.0 | ±4.5 | ±2.0 | ±6.5 | ±3.5 | ±3.7 | ±8.6 | ±8.0 | ±2.8 |

Control is after 1 month of commercial dog food only. Week 1 and 2 are after 1 and 2 weeks of ground beef supplementation (0.5 kg/day/dog) respectively.
*Denotes statistical significance at $p \leq 0.05$
**Denotes statistical significance at $p \leq 0.01$ The data in Table 2 indicates that the plasma L-Carnitine concentration of a normal, otherwise healthy dog, previously maintained on a commercial pet food diet, is substantially deficient in carnitine as compared with the plasma carnitine levels found in other mammals. For example, in humans the mean value of plasma total carnitine is $59.3 \pm 11.9$ $\mu$M for males and $51.5 \pm 11.6$ $\mu$M for females. C. J. Rebouche and D. J. Paulson, *Carnitine Metabolism and Function in Humans*, 6 Ann. Rev. Nutr. pp. 41-66, at page 45. In rats, plasma carnitine concentration averages $56.5 \pm 2.2$ $\mu$M. P. R. Borum, "Regulation of the Carnitine Concentration in Plasma" in *Carnitine Biosynthesis, Metabolism, and Functions*, 1980, Academic Press, New York, at page 119.

Further, the data of Table 2 indicates that the plasma total L-Carnitine concentration is significantly increased if the animal's diet is supplemented with L-Carnitine and that such level stabilizes in a range that is considered normal when compared with the plasma carnitine levels of other mammals. See Rebouche, supra, and Borum, supra.

It is clearly evident from the foregoing data that supplementation with a prophylactic amount of L-Carnitine of the standard commercial dog food will dramatically increase the plasma concentration of L-Carnitine in dogs. A prophylactic amount is the amount of L-Carnitine required to prevent the animal from developing a diet-induced carnitine deficiency. For a carnivore, such as a dog or cat, this is roughly equivalent to the amount of L-Carnitine the animal would ingest if its diet consisted of red meat, i.e., approximately 700 mg. of L-Carnitine per kilogram of food consumed.

Although the foregoing example details the use of raw frozen lean ground beef as a L-Carnitine source, the use of raw meat as a dietary supplement for pets is not advisable. Meat, particularly raw meat should not be fed to a pet because of the danger of transmitting parasites. In addition, meat provides excess protein which can cause and promote the progression of renal damage. Renal failure, after cancer, is the leading accidental cause of death in dogs. Lewis, et al., *Small Animal Clinical Nutrition III*. Chapter 2, pp 9–12, Mark Morris Associates, Topeka, Kans., 1987. The teachings of this article are incorporated herein by reference.

The preferred method of supplementation would be to administer commercially prepared L-Carnitine such as that obtained from Austin Chemical Company, Inc. 955 West Bryn Mawr Avenue, Rosemont, Ill.

These L-Carnitine supplements may be administered separately in the form of dietary supplements or they may be added at the time of manufacture of the commercial dog food as an additional ingredient in the commercial dog food. If used as a separate dietary supplement, the L-Carnitine may be combined with other valuable nutritional or prophylactic substances. Examples of this would be a combination of L-Carnitine with a vitamin and mineral preparation. Another example would be the inclusion of a prophylactic amount of L-Carnitine with an anti-heartworm medication such as diethyl-carbamazine.

The L-Carnitine supplement may also be administered as a liquid preparation. L-Carnitine is extremely soluble in water. Such a liquid preparation may be prepared by dissolving the appropriate amount of L-Carnitine in a waterbased solution. Flavoring agents or other nutritional or prophylactic substances may likewise be combined in the solution. The liquid preparation may be administered to the pet separately as a dietary supplement. It may be added to the pet's drinking water or to the animal's food. Further, the concentration of L-Carnitine in the liquid preparation may be such that it may be easily measured out and the prophylactic amount administered to the animal daily.

An alternative to administering daily a prophylactic amount of L-Carnitine to the pet, so as to avoid diet-induced carnitine deficiency, is the daily administration of a sufficient amount of gamma-butyrobetaine (GBB). GBB is the precursor of L-Carnitine in the biosynthetic pathway of the latter compound. See *Nutrition Reviews*, Vol. 36, No. 10, pp.305–309, 1978. The teachings of this article are incorporated herein by reference. It has been used successfully to alleviate carnitine deficiency syndromes in humans as described in U.S. Pat. No. 4,382,092 to Cavazza.

Applicants have found that administering GBB to a dog produces a concomitant use in serum L-Carnitine. See Table 3.

TABLE 3

Changes in serum L-Carnitine following oral administration of 5 grams of gamma-butyro-betaine. Amounts are given in $\mu M/l$.

|  | 0 hr. | 2 hr. | 4 hr. | 6 hr. |
|---|---|---|---|---|
| Free Carnitine | 15.8 | 60.2 | 51.4 | 45.0 |
| Esterified | 6.5 | 12.3 | 14.7 | 17.5 |
| Total Serum Carnitine | 22.3 | 72.5 | 66.1 | 62.5 |

In the preferred embodiment, sufficient GBB will be administered orally to the pet to raise the serum L-Carnitine level to 40.0 $\mu M$/liter of plasma. Administration can be accomplished in the manner described above for L-Carnitine, but the amount of GBB needed for the same amount of rise in serum L-Carnitine will be greater. In practice, between 1 to 5 grams of GBB should be administered daily, with the preferred amount being between 3–4 grams of GBB.

The use of GBB in lieu of L-Carnitine as a supplement provides a distinct economic advantage as the industrial preparation of GBB is less complicated and less expensive than the preparation of L-Carnitine. The L-Carnitine preparation requires the optical antipode resolution of the racemic mixture which is unavoidably obtained in the chemical synthesis of carnitine which necessarily increases the complexity and the expense.

The embodiments of the invention in which an exclusive property or privilege is claimed are defined as follows:

1. A method for preventing diet-induced carnitine deficiency in a domesticated dog or cat, comprising the step of: administering daily to said dog or cat a prophylactic amount of gamma-butyrobetaine.

2. A method as described in claim 1, wherein said gamma-butyrobetaine is administered by adding said prophylactic amount of gamma-butyrobetaine to a dog or cat food so as to form a mixture and daily feeding said mixture to said dog or cat.

3. A method as claimed in claim 2, wherein said mixture has a gamma-butyrobetaine concentration of at least 1.0 gram gamma-butyrobetaine per kilogram mixture.

4. A method as described in claim 1, wherein said gamma-butyrobetaine is administered by dissolving said prophylactic amount of gamma-butyrobetaine in water so as to form a solution and feeding said solution daily to said dog or cat.

5. A method as claimed in claim 4, wherein said solution has a gamma-butyrobetaine concentration of at least 1.0 gram gamma-butyrobetaine per liter of solution.

6. A method as claimed in claim 1, wherein said prophylactic amount is an amount sufficient to produce in said dog or cat a plasma total carnitine concentration of at least 40.0 $\mu M$/liter of plasma.

7. A method for preventing diet-induced carnitine deficiency in a domesticated dog or cat comprising the steps of: mixing a sufficient amount of gamma-butyrobetaine with a dog or cat foot so as to form a mixture having a gamma-butyrobetaine concentration of at least 1.0 gram per kilogram of mixture; feeding daily said mixture to said dog or cat.

* * * * *